Figure 1C:
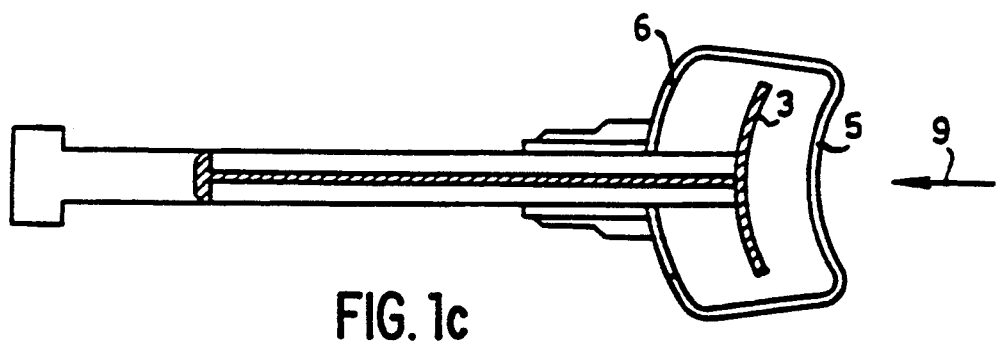

United States Patent [19]

van den Haak

[11] Patent Number: 5,364,359
[45] Date of Patent: Nov. 15, 1994

[54] SYRINGE WITH RETRACTABLE NEEDLE

[75] Inventor: Abraham van den Haak, Eesergroen, Netherlands

[73] Assignee: Advanced Protective Injection Systems Medical B.V., Esserogroen, Netherlands

[21] Appl. No.: 934,623

[22] PCT Filed: Mar. 1, 1991

[86] PCT No.: PCT/NL91/00035
§ 371 Date: Oct. 19, 1992
§ 102(e) Date: Oct. 19, 1992

[87] PCT Pub. No.: WO91/12842
PCT Pub. Date: Sep. 5, 1991

[30] Foreign Application Priority Data

Mar. 1, 1990 [NL] Netherlands ............... 9000487

[51] Int. Cl.⁵ ............... A61M 5/50; A61M 5/32; A61M 5/315
[52] U.S. Cl. ............... 604/110; 604/195; 604/228
[58] Field of Search ............... 604/192, 195, 196, 110, 604/228, 240, 242, 243, 225

[56] References Cited

U.S. PATENT DOCUMENTS

| | | |
|---|---|---|
| 4,838,870 | 6/1989 | Haber et al. |
| 4,950,241 | 8/1990 | Ranford ............... 604/110 |
| 5,045,063 | 9/1991 | Spielberg ............... 604/110 |
| 5,116,319 | 5/1992 | van den Haak ............... 604/110 |
| 5,226,881 | 7/1993 | Pickhard ............... 604/110 |
| 5,226,882 | 7/1993 | Bates ............... 604/110 |

FOREIGN PATENT DOCUMENTS

| | | |
|---|---|---|
| 272035 | 6/1988 | European Pat. Off. |
| 340899 | 11/1989 | European Pat. Off. |
| 669910 | 4/1989 | Switzerland |
| WO8900432 | 1/1989 | WIPO |

Primary Examiner—John D. Yasko
Assistant Examiner—Adam J. Cermak
Attorney, Agent, or Firm—Kenyon & Kenyon

[57] ABSTRACT

A safety assembly for an injection syringe, which syringe consists of a liquid container arranged or to be arranged within a casing (10) and having a piston (17) shiftable therein, a piston rod unit (1) provided with an external actuating element (3) and coupled or to be coupled with the piston, a needle foot (20) latched or to be latched at the other end of the casing with a hollow needle (27) communicating or to be communicated with the interior of the liquid container, said piston rod unit being provided with means (13) for unlatching the needle foot and to couple it with the piston rod unit, in order to allow to retract said foot together with the needle into the casing. According to the invention the piston rod unit comprises two parts (3, 5) which are mutually movable in the axial direction, one part being formed by the piston rod (1) or being connected thereto, and the other one comprising an unlatching element (8, 13, 22).

4 Claims, 2 Drawing Sheets

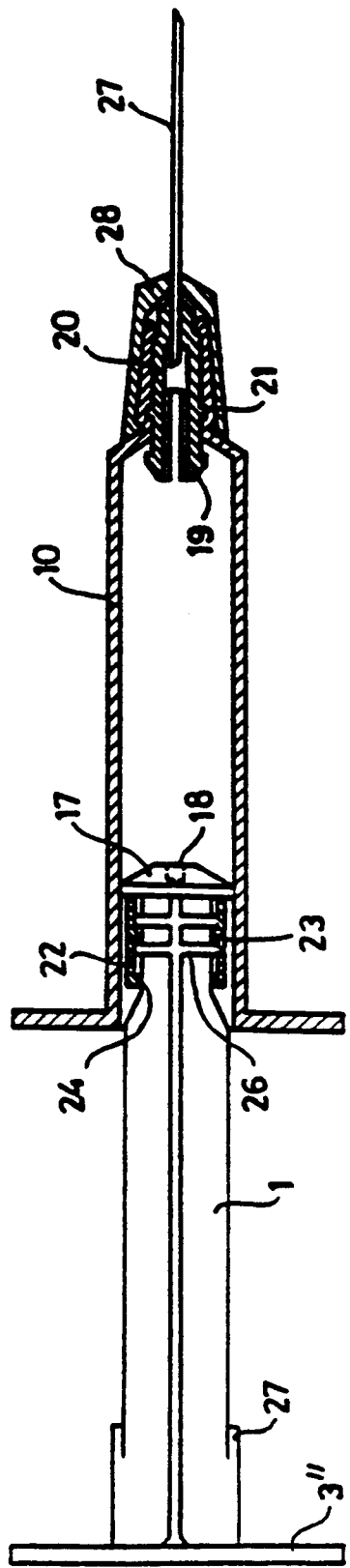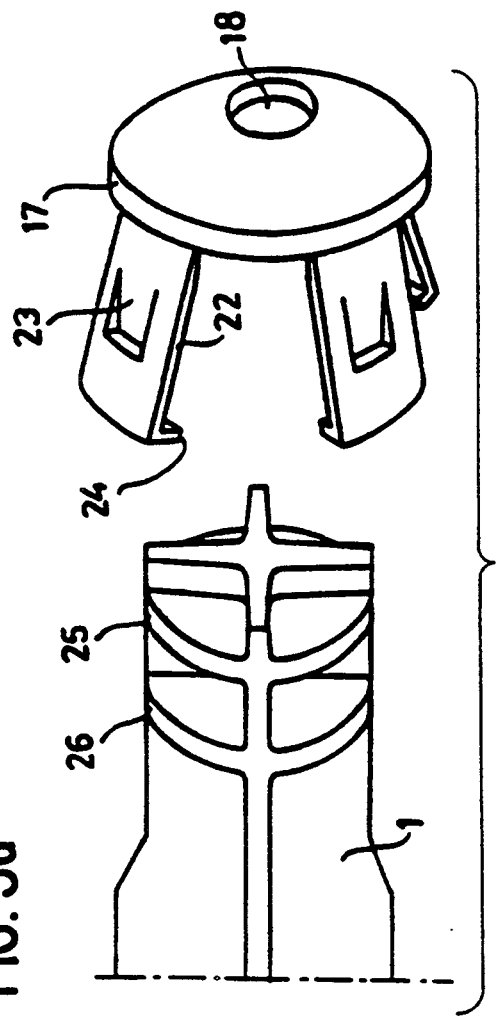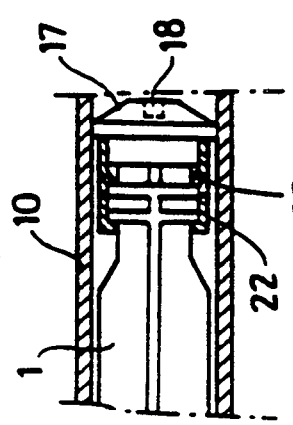
FIG. 3a
FIG. 3b
FIG. 3c

SYRINGE WITH RETRACTABLE NEEDLE

The invention relates to a safety assembly for an injection syringe, as defined in the preamble of claim 1.

Such injection syringes are known from EP-A 0 360 313 not published in time. Therein the needle can be fully retracted after use of the syringe, and can be bent if desired, in order to prevent effectively injures by the needle and re-use of the syringe.

It is an object of the invention to improve such syringes still more, in order to allow the injection liquid container to be partially emptied and/or to prevent refilling of this container before coupling the needle foot with the piston rod unit by retracting this unit. Moreover it is an object of the invention to prevent, in the case of such syringes which are to be filled before use with injection liquid by aspiration, that, when expelling air before aspiration, the piston rod unit will be coupled with the needle foot.

To that end the invention provides a safety assembly according to the characterizing portion of claim 1.

For obtaining the first object in injection syringes having an unlatching element which is shiftable outside the liquid container, the assembly according to the invention has the characteristics mentioned in claim 2 or 3.

For obtaining the second object in injection syringes having a piston rod unit which is or can be fixedly coupled with the piston, the assembly according to the invention has the characteristics of claim 4. For obtaining the third object, the assembly according to the invention has the characteristics of claims 5–8.

Figure 1A:
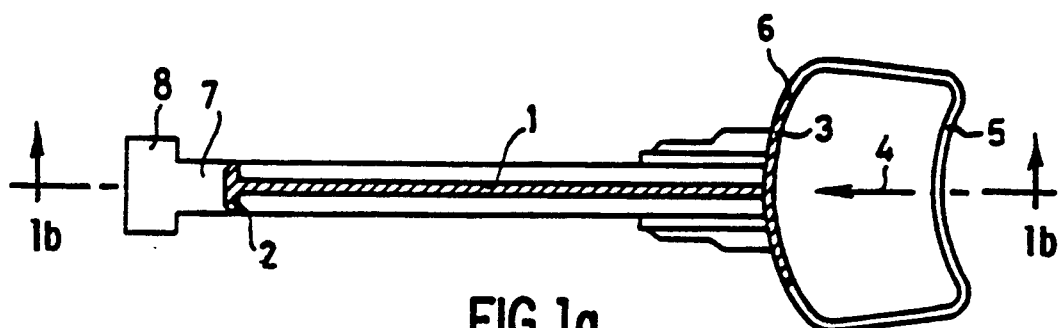
Figure 1B:
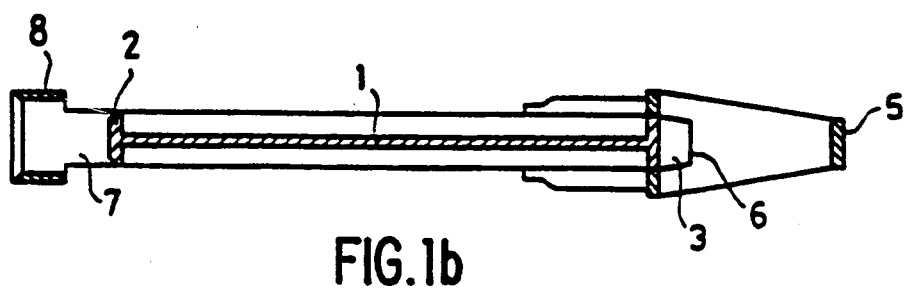
Figure 2:
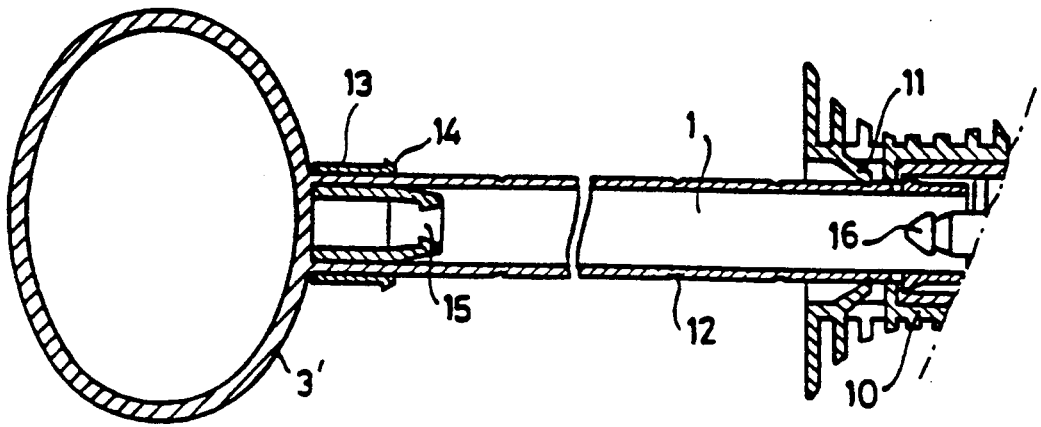

The invention will be elucidated below by reference to a drawing, showing in:

FIG. 1a a lateral view of a first embodiment of a piston rod unit according to the invention without the corresponding injection syringe;

FIG. 1b a cross-section according to line 1B—1B of FIG. 1a;

FIG. 1c a view corresponding with FIG. 1a of said unit in an other condition;

FIG. 2 a cross-section of an other embodiment of a piston rod unit according to the invention and of the adjacent terminal portion of a corresponding injection syringe;

FIGS. 3a and b a third embodiment of a piston rod unit in two different conditions; and FIG. 3c an exploded perspective view of a practical embodiment of the unit of FIGS. 3a and b.

In the drawing only those elements have been shown which are required for the description of the piston rod unit according to the invention. For the remaining parts of a corresponding injection syringe, reference can be made to EP-A 0 360 313, and in particular to the Figs. thereof to be mentioned below.

The unit according to the invention shown in FIG. 1 is intended to be used in injection syringes with separate liquid containers (so-called carpules) to be provided in a syringe casing, e.g. as shown in FIGS. 1 and 2 of the EP-application mentioned above.

In these known syringes, the liquid container is provided with a piston, and is closed, at the other extremity, by a plug which will be pierced by the inner end of an injection needle when a needle foot is placed on this extremity. This needle foot is latched in the syringe casing. When the piston is completely pushed into the liquid container by means of a piston rod unit, and the complete contents thereof are driven outwards through the needle, a sleeve which is shiftable around this container and which forms a part of this unit engages the needle foot and latching means thereof, the latter then being released, and the foot will be coupled with this sleeve in order to allow it to be pulled into the casing. Such syringes are used specially by dentists.

If, however, only a part of the contents of the container are to be used for an injection, the remainder thereof should be driven out before the coupling with the needle foot can take place. In order to avoid this objection, the piston rod unit of FIG. 1 can be used.

This unit comprises, to that end, and in the manner known from the EP-application mentioned above, a piston rod 1, e.g. with a cross-shaped cross-section, one extremity thereof joining a disc 2 or the like engaging the piston. At the other extremity, this rod 1 is provided with a pressing element 3, on which a pressure can be exerted by means of the thumb, as indicated by an arrow 4 in FIG. 1a.

This pressure element 2 forms the bottom of an eye 5, the terminal edges 6 thereof gripping behind the edges of the pressure element 3, so that, when pressing on the pressure element 3, the eye 5 is taken along, and, moreover, when the thumb pulls in the opposite sense of the arrow 4 on the eye 5, the pressure element 3 will be pulled along with the eye 5. The eye 5 is connected by means of connecting strips 7 with a coupling piece 8 which will engage the needle foot of the syringe when the unit has been completely pushed into the syringe casing and the liquid container has been emptied.

If, however, only a portion of the liquid contents of this container should be injected, the thumb, after this has taken place, will be taken from the eye and will be applied against the outer side of the eye 5, whereafter, as shown in FIG. 1c by an arrow 9, the eye 5 is pressed further inwards. Then the edges 6 of the eye 5 will release the pressure element 3, which, then, stays behind as shown. The sleeve 8 will, eventually, engage the needle foot, and the piston of the liquid container will no longer be displaced, so that the liquid remainder will remain therein.

In particular the eye 5 can be slightly flexible, so that, when pressing on the outer side, which is in particular concave, the edges 6 will deviate somewhat so as to simplify the release thereof.

In FIG. 2 an other unit according to the invention is shown, which is in particular intended for an injection syringe of, for instance, the type of FIG. 4 of the EP-application mentioned above, in which case the piston rod 1 is or can be fixedly connected with the piston of an injection syringe, and the piston rod of the piston is coupled with the needle foot at the end of its stroke.

However, if this coupling has not taken place, the piston can be retracted without taking along the needle foot, so that, then, the nearly emptied syringe might be refilled by aspiration through the hollow needle.

In order to prevent this, the casing 10 of the syringe is, at the terminal portion shown, at its inner side provided with elastic latching tongues 11 which cooperate with notches 12 of the piston rod 1 in such a manner that retraction of this rod by more than the mutual notch distance is prevented.

At the end of the rod 1 a pressure element or eve 3' is provided, and around the rod 1 and against this eye a sleeve is arranged with some friction, which is provided with a collar 14.

At the end of the stroke of the rod, the sleeve 13 arrives at the tongues 11 which will be pushed outwards, and will then grip behind the collar 14. At the same time a coupling with the needle foot has been obtained, for instance because internal claws 15 engage a knob 16 of the needle foot. When retracting the eye 3', the needle foot is taken along, but the sleeve 13 remains in the casing 10.

It will be clear that in the case of other needle foot coupling types, the same protection against retraction can be used. Also in the embodiment of FIG. 1 this protection can be used, and then the notches 12 can be provided in the portion connected with the eye 5 and the sleeve 8.

In FIG. 3 still another piston rod unit according to the invention is shown, which is, in particular, intended for an injection syringe according to FIG. 5 or 6 of the EP-application mentioned above.

The piston rod 1 of the considered unit is, at its outer extremity, provided with a pressure element 3", and carries, at its other extremity, a piston 17, and the edge of a cavity 18 formed in its end face can, then, engage claws 19 of a needle foot 20 of the syringe 10, the claws 19 then being bent, and latching lugs 21 being released and the foot 20 being unlatched This piston 17 is, in the present case, and as appears more clearly from FIG. 3c, provided with rearwardly extending tongues 22, which form a unitary structure with the piston 17. In the middle portion of each tongue an elastic lip 23 is bent inward, and the free extremity of each tongue has an inwardly directed thickened terminal rim 24. These lips 23 and terminal rims 24 form first and second latching lugs. The adjacent end of the piston rod 1 is provided with two circumferential collars 25 and 26.

In the initial condition shown in FIG. 3a, the first latching lugs 23 extend into the space between the collars 25 and 26, and the second latching lugs 24 are situated at some distance beyond the second collar 26. These lugs form a connection between the piston 17 and the piston rod 1 as soon as the piston is inserted into the injection syringe 10, so that the tongues 22 cannot be bent outwards anymore.

When a pressing force is exerted on the pressure element 3", in order to expel the air after inserting the needle through the plug of an injection liquid container, this pressing force is transmitted by the collar 26 towards the ends of the lips of the first latching lugs 23. The distance between the piston 17 and stops 27 arranged near the pressure element 3" for delimiting the piston stroke is such that, when fully inserting the piston rod 1, the piston head with the cavity 18 will just not reach the claws 19 of the needle foot 20, so that no coupling with the needle foot 20 can take place.

In order to suck in injection liquid into the injection syringe, the piston rod 1 is retracted. The lips 23 will now slide along the collar 25, after which their extremities will snap behind the other surface of this collar as shown in FIG. 3b. At the same time the second latching lugs or terminal rims 24 have reached the second collar 26. The piston 17 is now coupled with the rod 1 for both pulling and pressing forces, which coupling cannot be disrupted again.

The length of the piston rod/piston unit has now been increased sufficiently so that, when pushing inwards the piston 17 afterwards, a coupling with the needle foot 20 can be obtained, and the latter can be retracted then into the syringe 1. It is, of course, also possible to provide additional locking means for preventing the complete removal of the piston 1 from the syringe 10 and making the syringe re-usable thereafter.

The unit of FIG. 3 is, in the first place, intended for syringes in which the aspiration of injection liquid takes place through a needle 27 fixed in the foot 20, the needle being provided with a cap 28 from which the needle can be retracted through the foot 20. It is also possible to put a wider aspiration needle on the end of the syringe, and to replace it afterwards by an injection needle provided with a fitting adapted to the foot 20, which fitting will be retracted together with the foot 20.

In this embodiment, sterile air is present in the syringe, which, after inserting the needle into an injection liquid container, will be expelled into this container, so that no contamination of the contents thereof can take place.

It will be clear that the assembly of lugs 23, 24 and stops 25, 26 can be realised in many other ways, and should not necessarily be situated near the piston 17.

It is also possible to use a shiftable needle foot 20 (not shown) which, in the initial condition, is shifted so far outwards that no coupling with the piston can take place, and which, for instance by means of a snap lock which is released at a given pressure, is retained, and then the same lugs 21 may be used.

When putting on an aspiration needle, the foot 20 remains in this position. The injection needle fittings can be put on the extremity of the needle foot 20 and can be coupled therewith in order to be retracted afterwards together with the foot 20. When putting on the injection needle fittings, the needle foot 20 will be shifted towards the position shown in FIG. 3, so that coupling with the piston can take place. The aspiration needles have a fitting which cannot engage the foot 20, and will, therefore, not shift the foot.

I claim:
1. An injection syringe assembly comprising:
a casing having a first end and a second end;
a piston and a piston rod assembly capable of being inserted in said first end of said casing and shiftable in said casing;
a needle foot for supporting an injection needle and a latch for retaining said needle foot at said second end of said casing, wherein said needle foot is shiftable into said casing once said latch is unlatched;
means for unlatching said needle foot and for coupling said assembly to said needle foot at the end of a second inward stroke of said assembly;
means for restricting an inward stroke of said assembly, so that at the end of a first inward stroke said assembly stops a short distance from said needle foot so that said needle foot remains latched, and
means for decreasing said distance before a second inward stroke of said assembly so that at the end of said second inward stroke said needle foot is coupled to said assembly.

2. The syringe assembly according to claim 1 wherein said piston is connected to said piston rod by a piston latch comprising first and second sets of latching lugs and first and second latching collars, wherein said first set of latching lugs is movable relative to said first latching collar in one direction but not in an opposite direction so that said piston latch allows said piston to shift relative to said piston rod in one direction but not in an opposite direction, and wherein said shifting decreases said distance so that said needle foot may be coupled to said assembly at the end of said second inward stroke.

3. An injection syringe assembly comprising:

a casing having a first end and a second end;

a piston and a piston rod assembly capable of being inserted in said first end of said casing and shiftable in said casing;

a needle foot for supporting an injection needle and a latch for retaining said needle foot at said second end of said casing, wherein said needle foot is shiftable into said casing once said latch is unlatched;

wherein said piston and piston rod assembly comprises two parts which are movable with respect to each other, one part being formed by or connected to the piston rod, and the other part being formed by or connected to the piston and comprising means for unlatching said needle foot and for coupling said piston and piston rod assembly to said needle foot at the end of a second inward stroke of said assembly;

and said piston and piston rod assembly further comprising a piston latch comprising first and second sets of latching lugs and first and second latching collars wherein, in an initial condition, said two parts of said piston and piston rod assembly are mutually latched in a first position by said latching lugs and said latching collars so that said two parts do not shift relative to each other upon application of pressing forces exerted on said assembly during a first inward stroke of said assembly into said casing, in which first position the length of said assembly is insufficient for reaching the needle foot at the end of said first inward stroke; and wherein, upon a first outward stroke, said first set of latching lugs moves relative to said first latching collar so that said two parts shift relative to each other into a second position, in which second position the length of said assembly is sufficient for reaching the needle foot at the end of a second inward stroke of said assembly into said casing.

4. The injection syringe assembly according to claim 3, further comprising:

rearwardly directed tongues attached to said piston, wherein said first and second sets of latching lugs are located on said tongues, and wherein said first and second sets of latching lugs form a connection between the piston rod and the piston.

* * * * *

UNITED STATES PATENT AND TRADEMARK OFFICE
CERTIFICATE OF CORRECTION

PATENT NO. : 5,364,359
DATED : November 15, 1994
INVENTOR(S) : Abraham VAN DEN HAAK It is certified that error appears in the above-indentified patent and that said Letters Patent is hereby corrected as shown below:

In Column 2, line 65, change "eve" to --eye--.

Signed and Sealed this

Second Day of May, 1995

Attest:

BRUCE LEHMAN

Attesting Officer     Commissioner of Patents and Trademarks